United States Patent [19]

Rohrberg

[11] Patent Number: 5,474,064

[45] Date of Patent: Dec. 12, 1995

[54] BREAST SELF-EXAMINATION FLOATATION SYSTEM

[76] Inventor: Roderick G. Rohrberg, 2742 W. 234th St., Torrance, Calif. 90505

[21] Appl. No.: 123,490

[22] Filed: Sep. 17, 1993

[51] Int. Cl.⁶ ................................. A61B 5/00; A61B 8/00
[52] U.S. Cl. ...................... 128/630; 128/660.01; 128/915
[58] Field of Search ............................... 128/660.01, 630, 128/653, 915, 662.03; 4/485

[56] References Cited

U.S. PATENT DOCUMENTS

| | | | |
|---|---|---|---|
| 4,130,112 | 12/1978 | Frazer | 128/915 |
| 4,135,497 | 1/1979 | Meyers et al. | 128/736 |
| 4,347,850 | 9/1982 | Kelly-Fry et al. | 128/915 |
| 4,873,982 | 10/1989 | Morrison | 128/630 |

FOREIGN PATENT DOCUMENTS 2111347  6/1983  United Kingdom ................... 128/915

OTHER PUBLICATIONS

Echo scan Brochure—pp. 1–4, Metrix, Inc., P.O. Box 223 Deerfield, Illinois.

*Primary Examiner*—Francis Jaworski
*Attorney, Agent, or Firm*—Anglin & Giaccherini

[57] ABSTRACT

Apparatus and methods for assisting a person perform a self-examination of various body parts including the breasts (B) are disclosed. One of the preferred embodiments of the invention is designed to be used in the privacy of the home shower, either in a standing or seated position. A preferred embodiment (10) includes a pouch ring (12) attached to both a back panel (13) and to the upper portion (14a) of a generally cylindrical, flexible and waterproof retainer pouch (14). The pouch (14) is designed to hold a volume of fluid against the torso below the breasts (B). Although many different fluids may be used to implement the invention, the preferred embodiment of the invention utilizes water (W). Shoulder straps (16) connected to the pouch ring (12) help to bear the weight of the water (W) from the shower head (SH) which fills the pouch (14). The shoulder straps (16) may each include two sections (17) of Velcro™ fabric which make the device (10) easier to wear. A pair of support hooks (18) extending from the front of the pouch ring (12) are designed to engage a set of similar but inverted hooks (H) that are mounted on the shower wall (SW) below the shower head (SH). The lower portion (14b) of the pouch (14) is gathered together and enclosed by two ends (20a) and (20b) of a closure belt (20) which extends from the back panel (13). After the pouch (14) is secured around the torso and the user enters the shower, water (W) from the shower head (SH) fills the retainer pouch (14). The pouch (12) need only contain as much water (W) as is necessary to partially immerse the breasts (B). The buoyant force of the water (W) lifts the breasts (B) and permits them to assume a symmetric shape that is not distorted by the downward force of gravity. The floatation of the breast (B) permits the user to examine the breast (B) from many different directions. The user is able to comfortably reach into the pouch (14) through the opening (15) defined by the pouch ring (12), and then gently uses her fingertips to apply pressure around the breasts (B) in an effort to detect nodules or lumps.

21 Claims, 6 Drawing Sheets

BREAST SELF-EXAMINATION FLOATATION SYSTEM

FIELD OF THE INVENTION

The present invention relates to the field of health care devices. More particularly, this invention provides apparatus and methods that allow women to examine their breasts for abnormalities at home, in the doctor's office or at a health clinic.

BACKGROUND OF THE INVENTION

According to a recent study by the American Cancer Society, 46,000 women in the United States will die in 1993 from breast cancer. (From the 1993 World Almanac, published by Pharos Books.) Recent advances in diagnostic techniques and surgical treatments have helped to reduce the mortality rate due to breast cancer, but this disease is still the third greatest cause of death among women in this country. A variety of mammographic systems which employ X-rays and ultrasound have been developed over the past few decades, but this equipment is generally very large, prohibitively expensive and requires a trained technician to operate them. As an example, the minimum price of an ultrasonic imaging system sold by Acuson of Mountain View, Calif. exceeds $200,000.

Several patents noted below disclose various systems that pertain to equipment that may be used for different kinds of medical diagnosis.

U.S. Pat. No. 4,206,763 issued to Pedersen discloses a device and a method for ultrasonic examination for carcinoma of the breast. Pedersen employs a compartment in which water is drawn upward by suction over the breast. An ultrasonic transducer then revolves around the breast to obtain complete 360° scans. A pleated flexible bag 12 pulls the breast into a water bath compartment 4 when the water bath compartment 4 is evacuated by a pair of bellows 16. (See Column 1, Lines 60–68; Column 3, Lines 23–51 and Column 4, Lines 4 & 5.)

U.S. Pat. No. 4,252,125 issued to Iinuma describes an ultrasonic diagnosing apparatus that utilizes a receptacle 11 filled with warm water 12. An ultrasonic probe 14 makes an image of the breasts, which are pressed against a flexible membrane 18 that is stretched in front of the probe. (See Column 1, Lines 65–68 and Column 2, Lines 1–7.)

U.S. Pat. No. 4,341,222 issued to Gardineer et al. relates to a patient support system for orienting a woman's breast over an ultrasound scanner. The patient is shown bent over a pool of water 20 that is positioned over a scanning transducer 14. (See Column 5, Lines 62–68 and Column 6, Lines 1–4.) The water serves as a transmission medium for the ultrasonic waves. (See Column 2, Lines 15 & 16.)

U.S. Pat. No. 4,347,850 issued to Kelly-Fry et al. discloses a direct water coupling device for ultrasound scanning. A tank 10 is placed in a sealed position about the perimeter of the breast area while the patient is in a supine position. (See FIG. 3 & Column 4, Lines 37–38.)

U.S. Pat. No. 4,545,385 issued to Pirschel describes an apparatus for ultrasonic examination of body parts using a fluid container and an ultrasound scanning system. (See FIG. 1.) A liquid-filled basin 6 serves as an acoustic coupling. (See Column 3, Lines 4–5 & Column 3, Lines 24–25.)

U.S. Pat. No. 4,657,021 issued to Perry et al. concerns an apparatus which he claims enhances the sense of touch when placed between the fingertips of the user and the object being touched. A liquid lubricant 13 is captured inside a sealed enclosure 10 made from a pliable, elastic material. (See Column 2, Lines 36–40 and Column 3, Lines 4–18.)

U.S. Pat. No. 4,873,982 issued to Morrison contains a discussion of an examination garment that may be used to feel for lumps under the skin. (See FIGS. 1 and 3.)

U.S. Pat. No. 4,917,096 issued to Englehart et al. reveals the details of a portable ultrasonic probe. A fluid-filled enclosure is coupled to a handled portion which houses a drive motor. (See FIG. 3.) The probe 20 includes a fluid-filled enclosure 34. (See Column 4, Lines 30–31.)

The problem of providing a low-cost yet effective device for breast self-examination has presented a major challenge to medical technicians and imaging experts. The development of a device that enhances the prospects of detecting abnormalities during periodic breast self-examinations would constitute a major technological advance and would satisfy a long felt need within the health-care field.

SUMMARY OF THE INVENTION

The present invention can be used at home, in the doctor's office, or in a health clinic by women to perform periodic self-examination for breast abnormalities. One of the preferred embodiments is designed to be worn while standing upright in the shower. Once the device is donned by the woman, water from the shower head fills the pouch and her breasts are substantially immersed in a pool of water. The buoyant forces supplied by the water substantially counteract the forces of gravity and levitate the breasts. This levitation enhances the user's ability to detect the presence of a growth or tumor.

One of the embodiments of the floatation device includes a generally circular plastic pouch ring that is attached to the upper portion of a generally cylindrical plastic retainer pouch. This pouch holds approximately two and one half gallons of water which weighs about twenty pounds. The weight of the water is borne by a pair of shoulder straps which are attached to the pouch ring. The weight of the water is also supported by a pair of hooks that extend away from the front of the retainer pouch. These hooks are designed to engage a set of matching hooks mounted on the wall of the shower below the shower head. The lower portion of the device extends around the sides of the chest from a back panel at the rear of the device and terminates on either side in a closure belt. This belt buckles in front below the breasts over the lower portion of the retainer pouch, and forms a generally water-tight seal that maintains the pool of water in the pouch. The user performs the self-examination manually by reaching into the opening defined by the pouch ring, and then gently probes the breast tissue for lumps or nodules.

Enhanced embodiments of the invention may include an ultrasonic transducer and a receiver that would be able to produce an image of a growth or tumor. This embodiment might be used in a doctor's office or clinic as a precursor to the use of much more expensive mammographic X-ray equipment. Another enhancement features a vibrator which improves the tactile sensitivity of the fingertips when the breasts are examined. A lubricant may be added to the water to further improve tactile sensitivity. Salt may be added to the water to amplify the buoyant forces which lift the breasts.

Other embodiments utilize upright flames that may be employed in a shower stall to bear the weight of the pool of water. The flexible pouch can also be replaced by a molded plastic pouch that is used in conjunction with a cloth or plastic skirt. Yet another embodiment features a full-body floatation box that may be used to examine other body parts for abnormalities.

Each of these embodiments is inexpensive, easy to use and may be employed in the privacy of the home shower. The invention provides a non-invasive, painless and effective means of improving the chances of finding a breast tumor while it is in its early stages of growth.

An appreciation of other aims and objectives of the present invention and a more complete and comprehensive understanding of this invention may be achieved by studying the following description of a preferred embodiment and by referring to the accompanying drawings.

A DETAILED DESCRIPTION OF PREFERRED EMBODIMENTS

Figure 1:
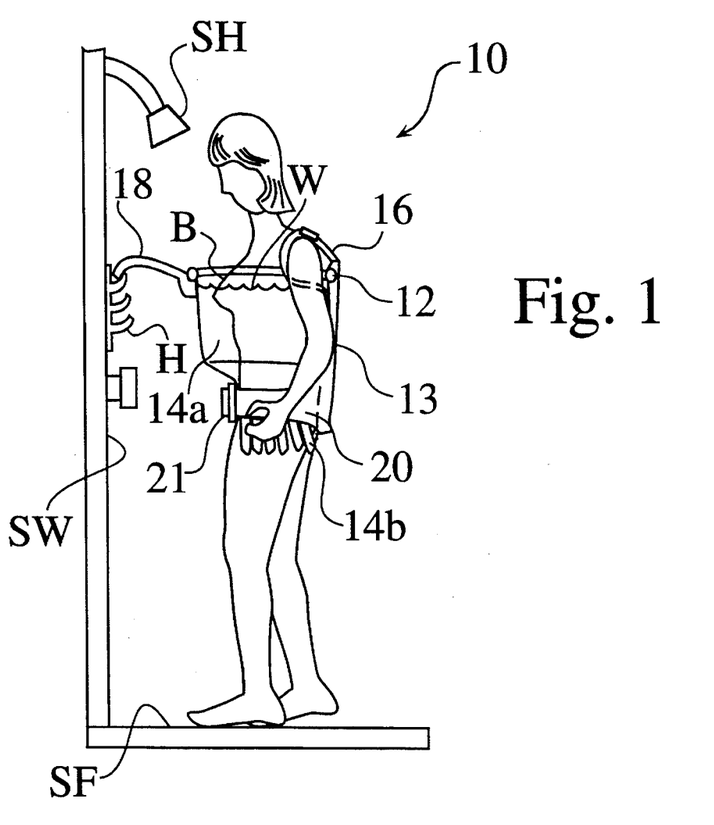
FIG. 1 is a side view of a woman using one of the preferred embodiments of the "Breast Self-Examination Floatation System".
Figure 2:
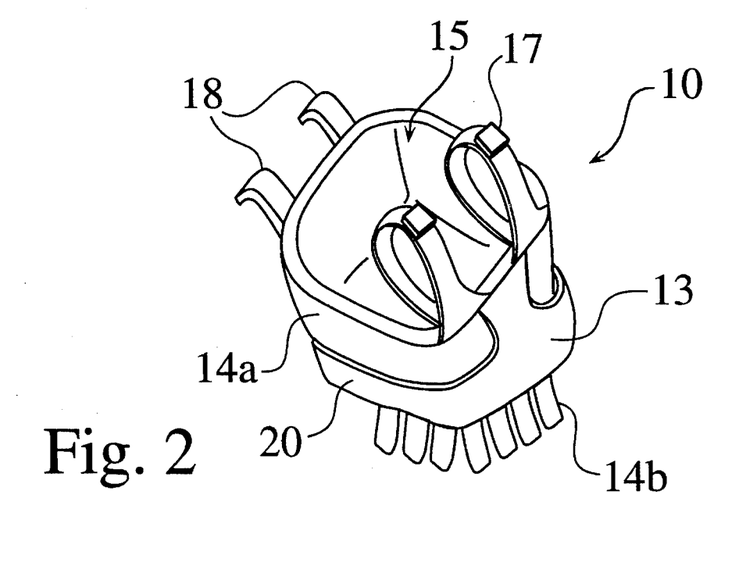
FIG. 2 is a perspective view of the device shown in FIG. 1.

FIG. 1 provides a schematic view of a woman using the Breast Self-Examination Floatation Device 10 in a shower stall. The preferred embodiment is designed to be used when the user is in a standing, upright or seated position. FIG. 2 supplies a perspective view of the embodiment shown in FIG. 1. The device 10 includes a pouch ring 12 attached to a back panel 13 and to the upper portion 14a of a generally cylindrical retainer pouch 14. The pouch 14 is designed to hold a volume of fluid against the torso below the breasts B. Although many different fluids may be used to implement the invention, the preferred embodiment of the invention utilizes water W. Shoulder straps 16 connected to the pouch ring 12 help to bear the weight of the water W from the shower head SH which fills the pouch 14. The shoulder straps 16 may each include two sections 17 of Velcro™ fabric which make the device 10 easier to wear. A pair of support hooks 18 extending from the front of the pouch ring 12 are designed to engage a set of similar but inverted hooks H that are mounted on the shower wall SW below the shower head SH. The lower portion 14b of the pouch 14 is gathered together and enclosed by two ends 20a and 20b of a closure belt 20 which extends from the back panel 13. When the belt 20 is joined by the belt buckle 21, it forms a generally watertight seal which holds the water W in the pouch 14 above the belt 20. In the preferred embodiment of the invention, the pouch ring 12 and central panel 13 are fabricated from plastic.

The retainer pouch 14 may be made from any thin flexible material that is impermeable to water W. One good choice for the retainer pouch 14 is clear polyethylene. In general, the shape and composition of the pouch 14 are not critically important, as long as it is capable of holding a sufficient volume of water W to lift the breasts B and to make the self-examination process easier for the user. The pouch 14 may comprise any container means that is capable of substantially surrounding any body part that requires examination.

In the preferred embodiment, the water W in the pouch can weigh up to about twenty pounds. Since the weight of the water W that is required to impart buoyant forces on the breasts is substantial, some support means will generally be used to help support this downward force. The shoulder straps 16 and hooks 18 described above are two preferred enhancements that may be used in conjunction with pouch 14. The disclosure of these two particular enhancements is not intended to limit the scope of the invention. Any support means capable of counteracting the weight of the water W in the pouch 14 may be employed to implement the invention.

After the pouch 14 is secured around the torso and the user enters the shower, water W from the shower head SH fills the retainer pouch 14. The pouch 12 need only contain as much water W as is necessary to partially immerse the breasts B. The buoyant force of the water W lifts the breasts B and permits them to assume a symmetric shape that is not distorted by the downward force of gravity. The floatation of the breast B permits the user to examiner the breast B from many different directions. The user is able to comfortably reach into the pouch 14 through the opening 15 defined by the pouch ring 12, and then gently uses her fingertips to apply pressure around the breasts B in an effort to detect nodules or lumps.

Figure 3:
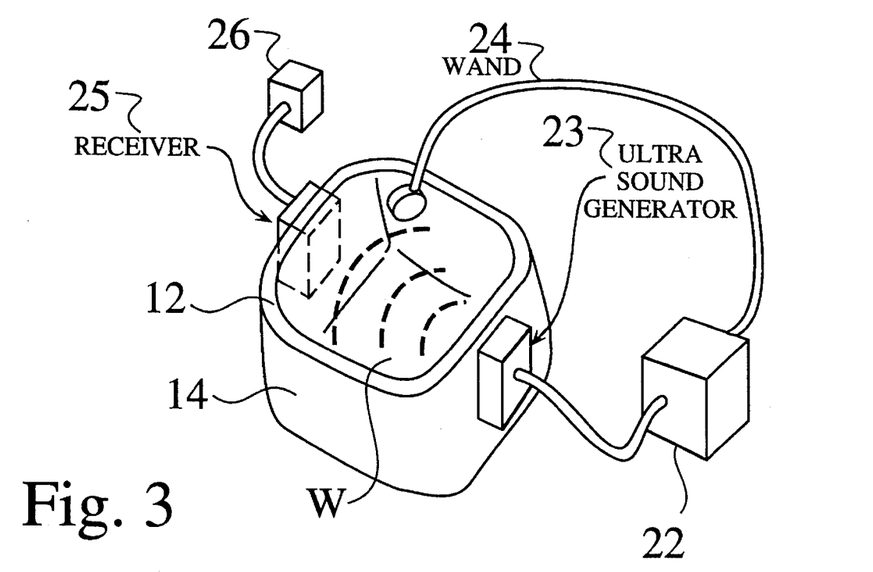
FIG. 3 is a schematic diagram that discloses a portion of an alternative embodiment of the invention which incorporates an ultrasonic imaging transducer and receiver.
Figure 4:
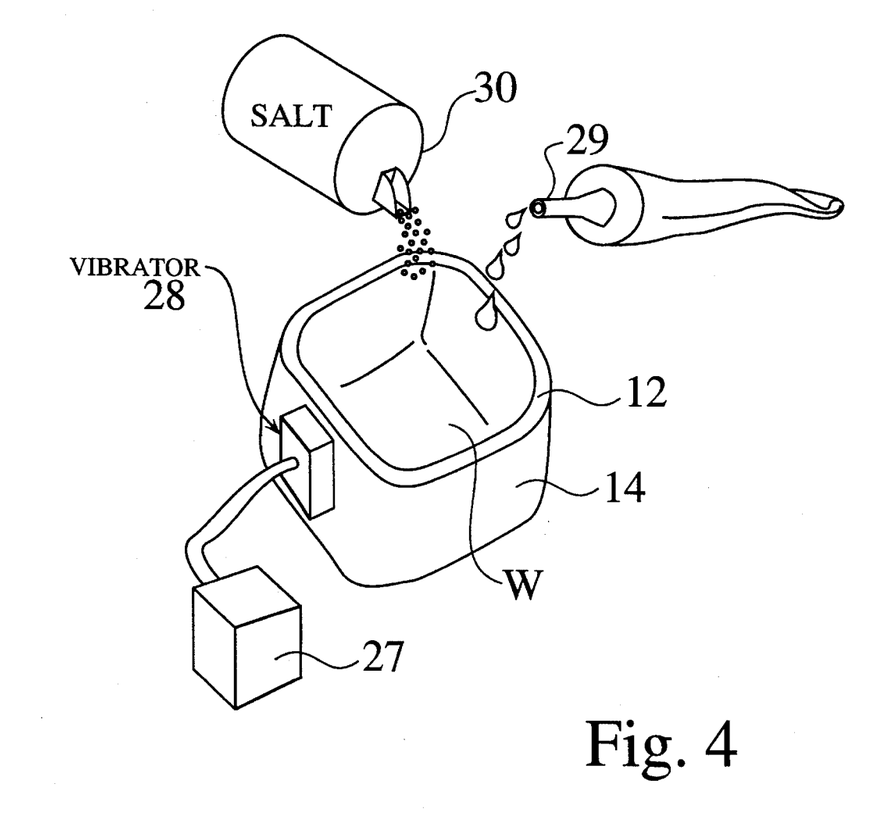
FIG. 4 is a schematic diagram that discloses a portion of an alternative embodiment of the invention which incorporates an electro-mechanical vibrator and a small volume of lubricant added to the pool of water that enhances the tactile sensitivity of the user's fingers during the examination process.

FIGS. 3 and 4 supply schematic views of enhanced versions of the preferred embodiment. FIG. 3 depicts a power supply 22 connected to an exterior ultrasound generator 23 affixed to the pouch 14 and an ultrasound wand 24 that may be immersed in the water W. Either the exterior generator 23 or the immersable wand 24 may be used to send ultrasound waves through the breast B. The ultrasound receiver 25 (which may also be located in the wand 24) detects waves after they transit through the breast B. Signal processing equipment 26 connected to the receiver 25 transforms the output signal from the receiver into an image that can be displayed or recorded on conventional imaging hardware. Conventional silicone jelly may be used as a coupling medium.

Alternatively, conventional X-Ray equipment may be employed to form an image of the breasts. An X-Ray source may be placed at any point around the periphery of the breast along with a section of film on the opposite side of the breast.

FIG. 4 reveals three additional methods of enhancing the prospects of detecting an abnormality through the use of the present invention. A power supply 27 and a vibrator 28 coupled to the retainer pouch 14 may be used to introduce a gentle vibration into the pool of water W. This slight vibration tends to enhance the user's sense of touch. Alternatively, the vibrator 28 can be strapped onto the palm of the user's hand. In some instances, it may be useful to place this hand-held vibrator over the sternum bone. In the preferred embodiment, the vibrator 28 is an electrically powered mechanical vibrator, but any means of generating vibrations in the pool of water would prove useful.

A small volume (usually a few drops) of lubricant 29 may be added to the water to help the fingertips slide over the breast B. In addition, a small volume of salt 30 (typically a few teaspoons) can be added to the water W to increase its salinity and density, and therefore increase the buoyant forces of the W on the breasts B.

Figure 5:
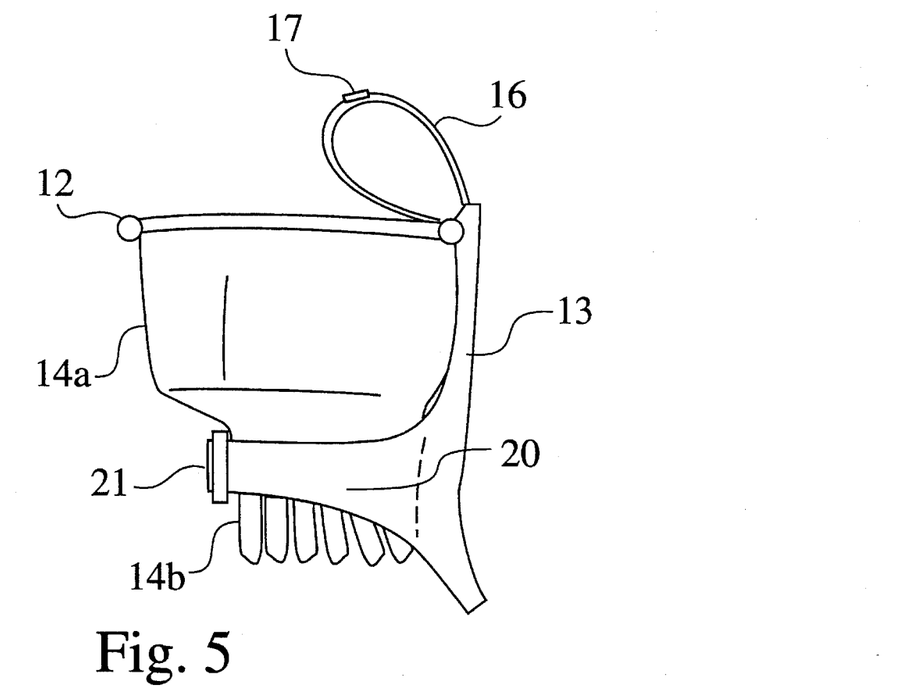
FIG. 5 is a side view of one of the preferred embodiments of the invention.
Figure 6:
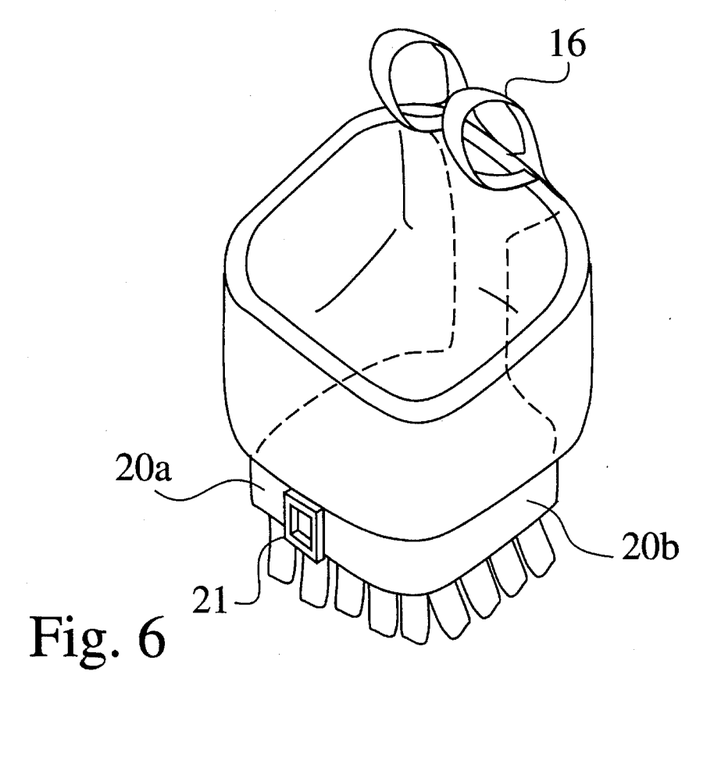
FIG. 6 reveals a perspective view of one of the preferred embodiments.
Figures 7, 8, 9:
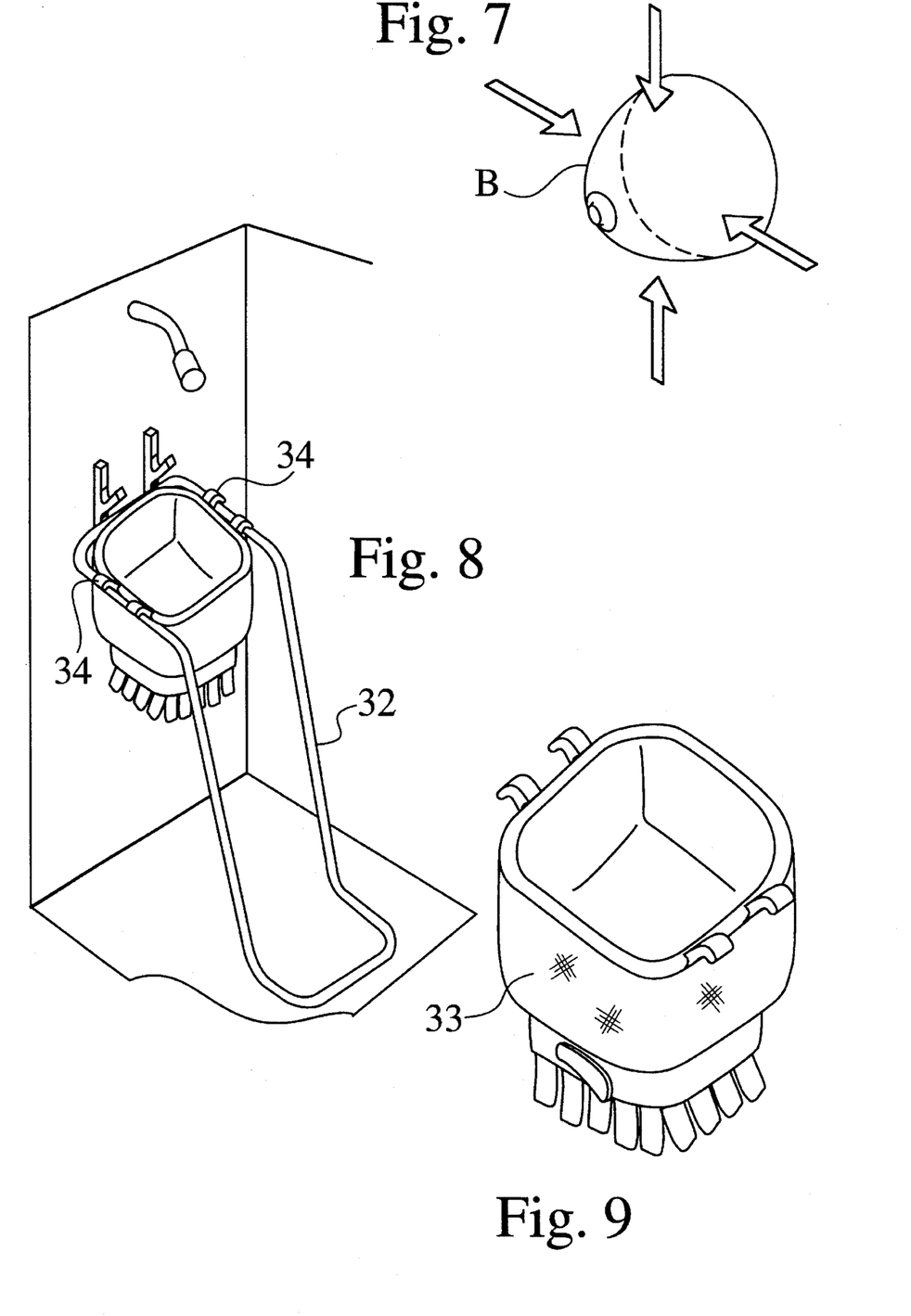
FIG. 7 presents a schematic view of a breast lifted by the buoyant forces of a volume of water.
FIG. 8 portrays a frame which can be used in a shower stall to support the weight of the water in the pouch.
FIG. 9 illustrates an alternative embodiment which incorporates a frame and a plastic or cloth bag.

FIG. 5 and 6 supply additional views of the invention. FIG. 7 is a schematic depiction of a female breast B, and reveals the symmetrical shape assumed by the breast B when supported by the buoyant forces of the water W in the pouch 14. The arrows in FIG. 7 suggest the various directions of approach of the fingertips during a self-examination.

FIG. 8 is a schematic illustration of a frame 32 that may be used in a shower. The retainer pouch 14 may be hung from this frame 32 using frame hooks 34. The frame 32 helps to support the weight of the water W and may obviate the need to wear the embodiment of the pouch 14 that incorporates shoulder straps 16. The frame 32 can be fabricated from metal, plastic or any other material that provides adequate structural support.

FIG. 9 is a perspective view of an alternative embodiment that includes a plastic or cloth bag 33.

Figure 10:
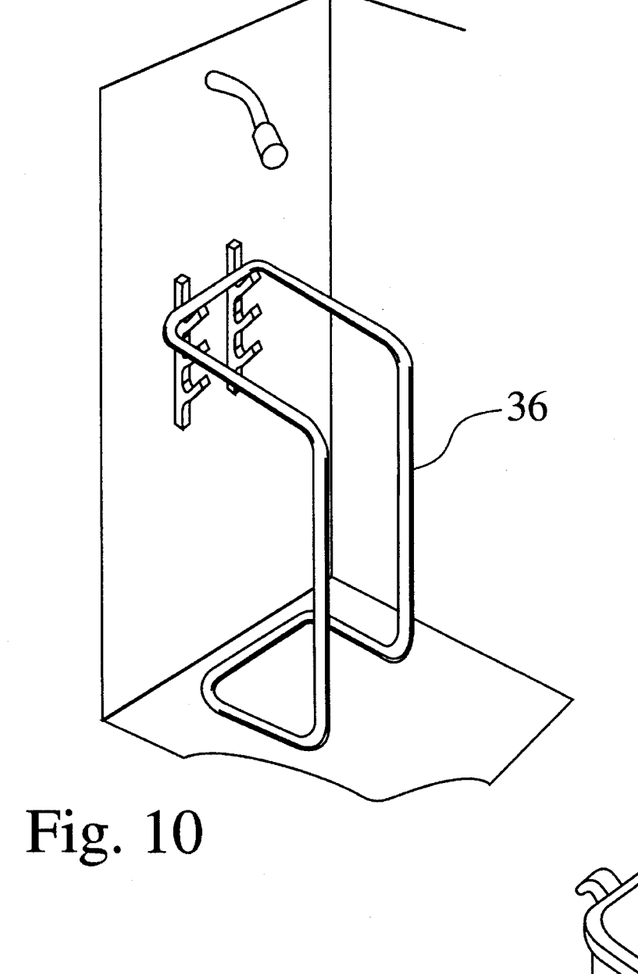
FIG. 10 shows another frame that may be employed in the shower.
Figure 11:
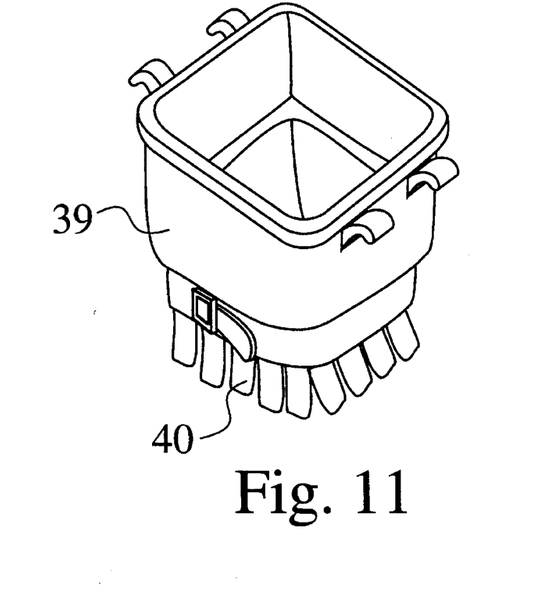
FIG. 11 exhibits an alternative embodiment of the pouch that comprises a molded pouch and a cloth or plastic skirt.

FIG. 10 shows a second support frame 36 that may be used in a shower. FIG. 11 shows an alternative container means for the water W, and comprises a molded plastic pouch 39 that can be used with a cloth or plastic skirt 40.

Figure 12:
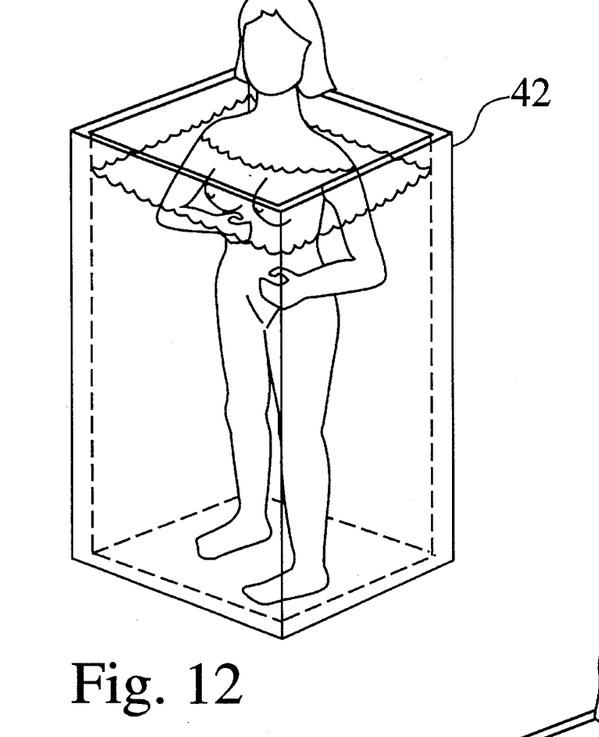
FIGS. 12 and 13 are schematic diagrams of full-body floatation boxes that can be used for examinations of other parts of the body.
Figure 13:
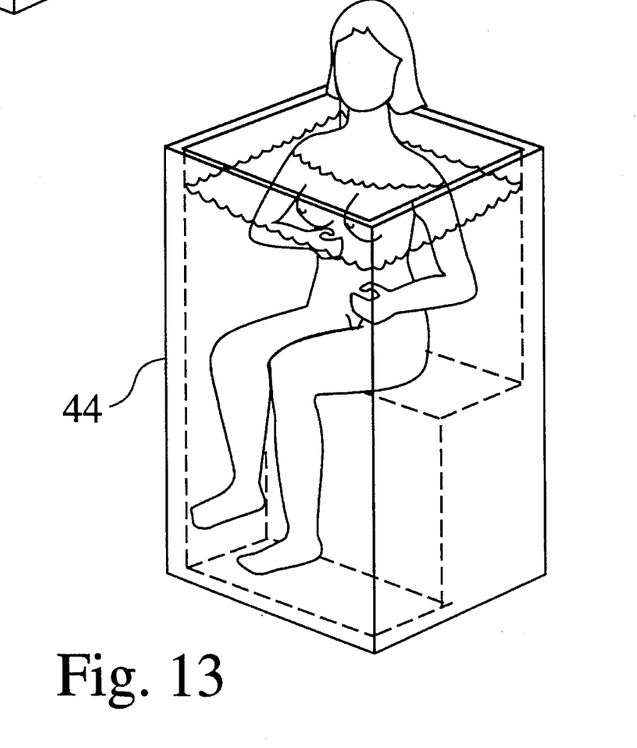

FIGS. 12 and 13 reveal full-body floatation boxes 42 and 44 that may be used for complete immersion of the body. The user may utilize these embodiments in a standing or a seated position, respectively. Yet another embodiment of the floatation box may enclose the user in a substantially reclining position.

ADVANTAGES OF THE INVENTION

The present invention comprises a straightforward system for assisting a woman or a man perform a self-examination of various body parts. The embodiments of the invention are relatively inexpensive, non-invasive, painless, and easy to use. Many of the embodiments may be used in the privacy of the user's home.

CONCLUSION

Although the present invention has been described in detail with reference to a particular preferred embodiment, persons possessing ordinary skill in the art to which this invention pertains will appreciate that various modifications and enhancements may be made without departing from the spirit and scope of the claims that follow. The various fabrication materials for the pouch ring 12, back panel 13, retainer pouch 14 and shoulder straps 16 that have been disclosed above are intended to educate the reader about one preferred embodiment, and are not intended to constrain the limits of the invention or the scope of the claims. The "List of Reference Characters" which follows is intended to provide the reader with a convenient means of identifying elements of the invention in the specification and drawings. This list is not intended to delineate or narrow the scope of the claims.

| LIST OF REFERENCE CHARACTERS | |
|---|---|
| 10 | Breast Examination Floatation Device |
| 12 | Pouch ring |
| 13 | Back panel |
| 14 | Retainer pouch |
| 14a | Upper portion of retainer pouch |
| 14b | Lower portion of retainer pouch |
| 16 | Shoulder straps |
| 17 | Velcro ™ fasteners |
| 18 | Support hook |
| 20 | Closure belt |
| 20a | First end of closure belt |
| 20b | Second end of closure belt |
| 21 | Belt buckle |
| 22 | Power supply |
| 23 | Ultra sound generator |
| 24 | Ultra sound wand |
| 25 | Ultra sound receiver |
| 26 | Signal processor |
| 27 | Power supply |
| 28 | Vibrator |
| 29 | Lubricant |
| 30 | Salt |
| 32 | Frame |
| 33 | Plastic or cloth bag |
| 34 | Frame hooks |
| 36 | Frame |
| 39 | Molded plastic pouch |
| 40 | Cloth or plastic skirt |
| 42, 44 | Full-body floatation box |
| B | Breast |
| H | Wall mounted hooks |
| P | Person |
| SF | Shower floor |
| SH | Shower head |
| SW | Shower wall |
| W | Water |

What is claimed is:

1. An apparatus for assisting a person in performing a self-examination of a portion of body tissue comprising:

a container for substantially surrounding a portion of said body tissue and for enclosing a volume of fluid; said container for holding said volume of fluid while said person is in an upright position;

said container including an opening;

said opening permitting said person to perform a self-examination of said portion of body tissue; said opening being large enough to permit said person to examine said portion of said body tissue using the fingers of the hand;

said volume of fluid being maintained adjacent to said portion of said body tissue to allow said portion of said body tissue to be levitated by the buoyant forces of said volume of fluid acting on said portion of said body tissue.

2. An apparatus as recited in claim 1, further comprising:

a support means adapted for attachment to said person for counteracting the weight of said volume of fluid and for maintaining said volume of fluid adjacent to said portion of body tissue.

3. An apparatus as recited in claim 2, in which said support means comprises a pair of shoulder straps (16).

4. An apparatus as recited in claim 3, in which each of said pair of shoulder straps (16) includes Velcro™ fasteners (17).

5. An apparatus as recited in claim 2, in which said support means comprises a support hook (18); said support hook (18) being attached to said container means.

6. An apparatus as recited in claim 2, in which said support means includes a sealing means for closing said support means against said person to hold said volume of fluid in said container.

7. An apparatus as recited in claim 1, in which said volume of fluid is a volume of water.

8. An apparatus as recited in claim 7, in which a volume of salt is added to said volume of water to increase the density of said volume of water.

9. An apparatus as recited in claim 1, in which a small volume of lubricant is added to said volume of fluid to enhance said person's tactile sensitivity to the detection of abnormalities in said portion of body tissue.

10. An apparatus as recited in claim 1, further comprising:
a vibration means for imparting a gentle oscillation to said volume of fluid to enhance said person's tactile sensitivity to the detection of abnormalities in said portion of body tissue.

11. An apparatus as recited in claim 1, further comprising:
an ultrasonic imaging means for detecting abnormalities in said portion of body tissue.

12. An apparatus as recited in claim 1, in which said container means is worn by said person while standing in an upright position.

13. An apparatus as recited in claim 1, in which said container means is worn by said person while seated.

14. An apparatus as recited in claim 1, in which said container means includes:
a pouch ring (12);
a back panel (13); said back panel (13) being attached to said pouch ring (12); and
a retainer pouch (14);
said retainer pouch (14) having an upper portion (14a) and a lower portion (14b);
said upper portion (14a) being attached to said pouch ring (12).

15. An apparatus for assisting a woman in performing a self-examination of a breast comprising:
a pouch ring (12);
a back panel (13); said back panel (13) being attached to said pouch ring (12); and
a retainer pouch (14);
said retainer pouch (14) having an upper portion (14a) and a lower portion (14b);
said upper portion (14a) of said retainer pouch (14) being attached to said pouch ring (12);
said retainer pouch (14) having an opening (15) located generally near said upper portion (14a);
said retainer pouch (14) being capable of fitting around a woman's torso and generally surrounding her breasts (B);
said retainer pouch (14) being impermeable to water (W);
a pair of shoulder straps (16); said shoulder straps (16) being attached to said pouch ring (12);
a support hook (18); said support hook (18) being coupled to said pouch ring (12);
a closure belt (20);
said closure belt (20) having a first end (20a) and a second end (20b);
said first and said second end (20a & 20b) of said closure belt (20) extending from said back panel (13) and over said retainer pouch (14);
said first and said second ends (20a & 20b) of said closure belt (20) being capable of being joined to form a substantially watertight seal around said lower portion (14b) of said retainer pouch (14);
said closure belt (20) enabling said retainer pouch (14) to be filled with a volume of water (W) and allowing said breast (B) to be substantially immersed in said volume of water (W).

16. A method of performing a self-examination of a breast comprising the steps of:
donning a container means for substantially surrounding said breast and for enclosing a volume of fluid; said container means including an opening; said opening being large enough to permit said person to permit said person to examine said portion of said body tissue using the fingers of the hand;
filling said container means with a volume of water; said container means for holding said volume of water while said person is in an upright position;
substantially immersing said breast in said volume of water to impart buoyant forces on said breast that counteract the force of gravity; and
examining said breast manually in an effort to detect an abnormality.

17. A method of performing a self-examination of a breast as recited in claim 16, further comprising the step of:
adding a volume of salt to said volume of water to increase the density of said volume of water and to increase the buoyant forces applied on said breast.

18. A method of performing a self-examination of a breast as recited in claim 16, further comprising the step of:
adding a volume of a lubricant to said volume of water to increase tactile sensitivity during self-examination.

19. A method of performing a self-examination of a breast as recited in claim 16, further comprising the step of:
vibrating said volume of water using an electro-mechanical vibrator attached to said container means.

20. A method of performing a self-examination of a breast as recited in claim 16, further comprising the step of:
forming an image of said breast using an ultrasonic transducer and receiver.

21. A method of performing a self-examination of a breast as recited in claim 16, further comprising the step of:
forming an image of said breast using X-Ray equipment.

* * * * *